United States Patent
Yagi et al.

(10) Patent No.: US 8,796,490 B2
(45) Date of Patent: Aug. 5, 2014

(54) METHOD OF PRODUCING A TRIARYLAMINE COMPOUND

(75) Inventors: Kazunari Yagi, Minami-ashigara (JP); Kazumi Nii, Minami-ashigara (JP)

(73) Assignee: Fujifilm Corporation, Minato-ku, Tokyo (JP)

(*) Notice: Subject to any disclaimer, the term of this patent is extended or adjusted under 35 U.S.C. 154(b) by 781 days.

(21) Appl. No.: 12/769,120

(22) Filed: Apr. 28, 2010

(65) Prior Publication Data

US 2011/0269994 A1 Nov. 3, 2011

(51) Int. Cl.
*C07C 211/00* (2006.01)

(52) U.S. Cl.
USPC .......................................................... 564/434

(58) Field of Classification Search
None
See application file for complete search history.

(56) References Cited

FOREIGN PATENT DOCUMENTS

JP 2007-178813 A 7/2007

OTHER PUBLICATIONS

Tian, Yu-Peng et al. Journal of Materials Chemistry (2007), 17(34), 3646-3654.*
Hartwig et al. J. Am. Chem. Soc. 2001, 123, 2677-2678.*
Beletskaya et al. Chem. Rev. 2000, 100, 3009-3066.*
Caulfield, D. Tappi Journal, 1994, 77(3), 205-212.*

* cited by examiner

*Primary Examiner* — Clinton Brooks
(74) *Attorney, Agent, or Firm* — Buchanan Ingersoll & Rooney PC

(57) ABSTRACT

A production method of a triarylamine compound including: producing a particular triarylamine compound by performing a reaction between a specific halogenated triarylamine compound and a specific olefin in the presence of palladium and alkylphosphine.

8 Claims, No Drawings

METHOD OF PRODUCING A TRIARYLAMINE COMPOUND

TECHNICAL FIELD

The present invention relates to a method of producing a triarylamine compound.

BACKGROUND ART

In recent years, organic devices using an organic compound in place of an inorganic material as a functional material are developed and are getting attention. The organic device is able to make an instrument as flexible as the instrument using the inorganic material is difficult to do so. Further, a significant weight saving of the instrument is made possible by the organic device. Further, the organic compound is easy to modify its chemical structure and to change a synthetic method. As a result, there is a lot of freedom in designing, whereby the possibilities for enhancement of production efficiency and reduction of production cost in mass production as well as improvement of material property are widely expanded. Taking these advantages, development of organic devices as a next generation device is actively moving forward, focusing on potable instruments, image-involved instruments or the like. Typical examples of the instruments include an organic electroluminescent element, an organic photoelectric conversion element, an organic transistor, a touch panel, and an electrophotography.

In the organic devices, a charge transporting material is used as a functional material for controlling their electrical or chemical behavior. With respect to the charge transporting material, a productive aptitude at the time when the charge transporting material is prepared or incorporated in the device is required in addition to basic properties such as charge transportation property and photostability. Further, a mechanical strength directly linked with durability at the time of use is also needed.

As a method of forming a thin film of organic material involved in the production of the organic device, a vacuum deposition method, a wet coating method and the like are proposed. However, the vacuum deposition method needs a large-scale machine. In contrast, the wet coating method can be carried out using simple equipments. Moreover, making of large area can be easily done by the wet coating method. For these reasons, the wet coating method is favorable from the viewpoint that a productive efficiency can be enhanced with a reduced cost, so that the wet coating method is a production method suitable for industrial-scale production. Accordingly, the charge transporting material is also desired to have a productive aptitude in the wet coating method. Specifically, a film is produced by coating a coating solution in which an charge transporting material including an organic material as a component is dissolved in a solvent, followed by removing the solvent. In the preparation of the coating solution, solubility of the charge transporting material with respect to the solvent is needed. Therefore, a technique in which various kinds of substituents are introduced into an organic compound that constitutes the charge transporting material is used (see Patent Literature 1).

Further, in order to enhance strength of the produced organic device, the Patent Literature 1 proposes to enhance a mechanical strength by the method of introducing a crosslinking group into an organic compound that constitutes the charge transporting material, and forming a coating film of this compound, followed by curing. As for the crosslinking group, an acrylic group and a methacrylic group are excellent in terms of crosslinking property and handleability. As a technique for introducing an acrylic group or a methacrylic group, a production method in which an acrylic acid or an acrylic acid halide and an alcohol product of a compound that constitutes an charge transporting material are subjected to condensation is a common method.

CITATION LIST

Patent Literature

[Patent Literature 1] JP-A-2007-178813

SUMMARY OF INVENTION

Technical Problem

However, in consideration of general synthetic method, it takes time and effort to get an alcohol product that is used as a raw material of the organic material that constitutes the charge transporting material. Further, a general-purpose compound can not be used as a substrate of the alcohol product. One example of the synthetic method is shown in the following scheme 1. Compound A-1 and compound A-2 each of which is used as a substrate are not a general-purpose compound. These compounds themselves need time and effort to synthesize or obtain them. Further, since a synthesis route to obtain compound 203 using these compounds is taken, some kinds of time, effort and complication are forced.

Thus, as a result of studies on a novel method of synthesizing a triarylamine compound that constitutes the charge transporting material, the present inventors address a proposal of the production method that can respond using convenient and general purpose materials.

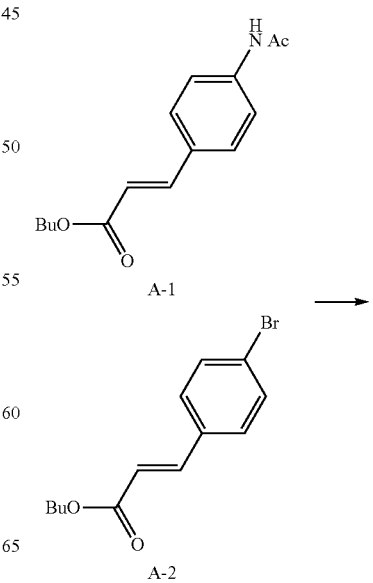

Scheme 1

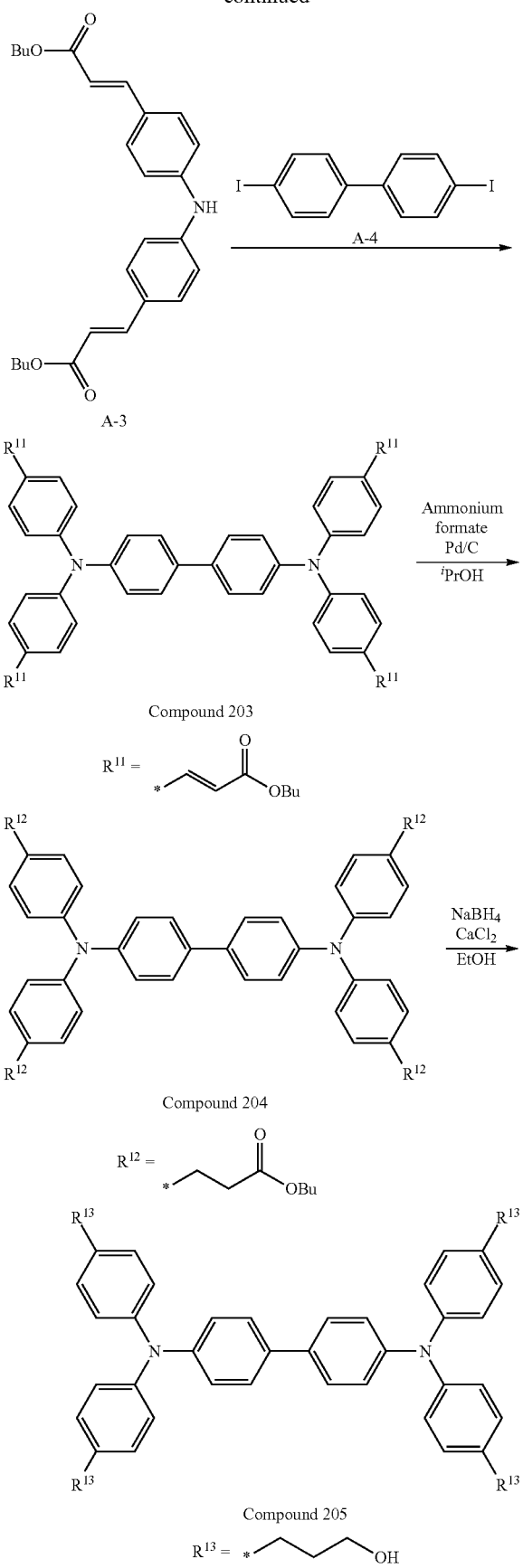

Et: Ethyl group
$^i$Pr: Isopropyl group
Bu: Normal butyl group
Ac: Acetyl group
*: Bonding part to a benzene ring In the mean time, a reaction for the synthesis of a styrene derivative by reacting aryl halide and an olefin compound is known. Generally, this reaction is called Heck reaction. This reaction does not progress if aryl halide has an electron-donating group (for example, O atom, N atom) as a substituent. Therefore, as a solution to address this problem and to progress the reaction, a method of using a combination of a palladium catalyst and tris (o-toryl) phosphine is proposed (see Clemence Allain et al., Chem Bio Chem., 2007, 8, p. 424). Further, a method of using a catalyst $(Pd[P(tBu)_3]_2)$ in which Palladium is coordinated with alkylphosphine is disclosed (see Md. A. Wahab et al., Chem. Mater., 2008, 20, p 1855). However, conversion of a residue of the olefin compound (olefin compound having a pyridyl group, or vinyl silane) introduced by these methods to an alcohol substituent is not easy to be conducted. As for the olefin compound capable of conducting the conversion immediately, introduction of α,β-unsaturated carbonyl substituent is needed. However, before now there is neither known method of effectively introducing the substituent nor known catalyst for the method.

In view of the above situation, the present invention addresses a provision of a method of producing a triarylamine compound, the method being capable of producing a triarylamine compound having an α,β-unsaturated carbonyl substituent that is an organic material useful for synthesis of an organic compound that constitutes the charge transporting material by simple and less number of processes omitting complicated processes; the method being capable of using a general purpose compound without a special substrate as a raw material; and the method being capable of suitably responding to an industrial-scale production of the charge transporting material.

Solution to Problem

The above-described problems have been addressed by the following means.
(1) A production method of a triarylamine compound, comprising the steps of:
providing a compound represented by following formula (1) and a compound represented by following formula (2);
allowing the compound represented by (1) to react with the compound represented by formula (2) in the presence of palladium and alkylphosphine, to form a compound represented by following formula (3).

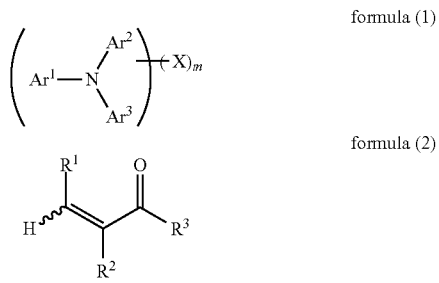

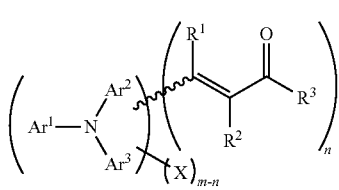 formula (3)

[In formula (1), $Ar^1$, $Ar^2$ and $Ar^3$ each independently represent an aryl group or a heteroaryl group, each of which may be substituted. X represents a halogen atom substituted onto $Ar^1$, $Ar^2$, and/or $Ar^3$. If a plurality of X is present, the plurality of X may be the same or different halogen atom from each other. m represents a natural number.]

[In formula (2), $R^1$, $R^2$ and $R^3$ each independently represent a hydrogen atom or a substituent.]

[In formula (3), $Ar^1$, $Ar^2$, $Ar^3$, X and m have the same meanings as those of formula (1), respectively. $R^1$, $R^2$ and $R^3$ have the same meanings as those of formula (2), respectively. n represents a natural number equal to or less than m.]

(2) The production method according to (1), wherein the compound represented by formula (1) is obtained by halogenation of a compound represented by following formula (4).

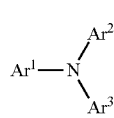 formula (4)

[In formula (4), $Ar^1$, $Ar^2$ and $Ar^3$ have the same meanings as those of formula (1), respectively.]

(3) The production method according to (1), wherein the compound represented by formula (1) is a compound represented by following formula (5).

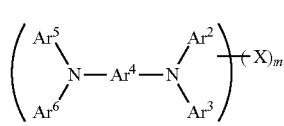 formula (5)

[In formula (5), $Ar^2$, $Ar^3$, X and m have the same meanings as those of formula (1), respectively. $Ar^5$ and $Ar^6$ each independently represent an aryl group or a heteroaryl group, each of which may be substituted. $Ar^4$ represents an arylene group or a heteroarylene group, each of which may be substituted.]

(4) A catalyst for production of a triarylamine compound, comprising: palladium and alkylphosphine, wherein the catalyst is used for a reaction between a compound represented by following formula (1) and a compound represented by following formula (2) to form a compound represented by following formula (3).

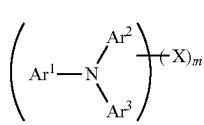 formula (1)

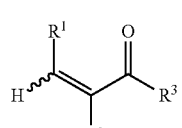 formula (2)

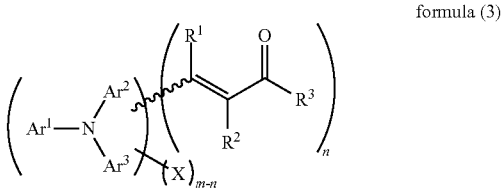 formula (3)

[In formula (1), $Ar^1$, $Ar^2$ and $Ar^3$ each independently represent an aryl group or a heteroaryl group, each of which may be substituted. X represents a halogen atom substituted onto $Ar^1$, $Ar^2$, and/or $Ar^3$. However, if a plurality of X is present, the plurality of X may be the same or different halogen atom from each other. m represents a natural number.]

[In formula (2), $R^1$, $R^2$ and $R^3$ each independently represent a substituent.]

[In formula (3), $Ar^1$, $Ar^2$, $Ar^a$, X and m have the same meanings as those of formula (1), respectively. $R^1$, $R^2$ and $R^3$ have the same meanings as those of formula (2), respectively. n represents a natural number equal to or less than m.]

(5) A production method of an charge transporting material having a crosslinking group, comprising the steps of:
producing the compound represented by formula (3) through the method according to (1), and
modifying the substituent represented by —C($R^1$)═C($R^2$)C(═O)$R^3$ of the compound represented by formula (3) to form the crosslinking group.

Advantageous Effect of Invention

According to the production method of a triarylamine compound of the present invention, it is possible to produce a triarylamine compound having an α,β-unsaturated carbonyl substituent that is an organic material useful for synthesis of an organic compound that constitutes the charge transporting material by simple and less number of processes omitting complicated processes. Further, a general purpose compound without a special substrate can be used as a raw material. The method is able to suitably address industrial-scale production of the charge transporting material.

Further, the catalyst of the present invention exhibits an excellent effect of rapidly-progressing the reaction to introduce α,β-unsaturated carbonyl substituent to a compound having a triarylamine skeleton in the production of an organic material useful for synthesis of an organic compound that constitutes the charge transporting material whereby an objective compound can be obtained in a high yield.

The above-described characteristics and other characteristics and advantages of the present invention will be apparent from the following descriptions.

BEST MODE FOR CARRYING OUT THE INVENTION

In the production method of the present invention, the above-described compound represented by formula (1) and the above-described compound represented by formula (2) are reacted in the presence of alkylphosphine and palladium to form the above-described compound represented by formula (3) Hereinafter, the present invention is explained in detail.

Firstly, it is explained that the catalyst enabling prompt progress of the above reaction in the production method of the present invention. The catalyst of the present invention for producing a triarylamine compound comprises palladium and alkylphosphine in combination.

With respect to the catalyst, when the palladium is used as a compound containing palladium, examples of a compound containing divalent palladium include palladium chloride, palladium bromide, palladium iodide, palladium acetate, palladium acetylacetonate, palladium hexafluoroacetylacetonate, palladium trifluoroacetate, allyl palladium chloride dimer, (2,2'-bipyridine)dichloropalladium, bis(benzonitrile)dichloropalladium, bis(acetonitrile)dichloropalladium, (bicyclo[2.2.1]hepta-2,5-diene)dichloropalladium, dichloro(1,5-cyclooctadiene)palladium, dibromobis(triphenylphosphine)palladium, dichloro(N,N,N',N'-tetramethylethylenediamine)palladium, dichloro(1,10-phenathroline)palladium, dichlorobis(triphenylphosphinepalladium), ammonium tetrachloropalladate, diaminedibromopalladium, diaminedichloropalladium, diaminediiodopalladium, potassium tetrabromopalladate, potassium tetrachloropalladate and sodium tetrachloropalladate; and examples of a compound containing zero-valent palladium include tetrakis(triphenylphosphine)palladium and tris(dibenzylideneacetone)palladium. Particularly, palladium acetate, palladium chloride, palladium acetylacetonate, bis(acetonitrile)dichloropalladium, tris(dibenzylideneacetone)palladium, allyl palladium chloride dimer are preferable; palladium acetate, bis(acetonitrile)dichloropalladium, tris(dibenzylideneacetone)palladium are particularly preferable.

In the present invention, the catalyst may be employed if it is the combination of palladium and alkylphosphine, and the embodiment of supplying it is not particularly limited. The examples may include: (i) the combination of the above palladium compound and alkylphosphine, (ii) a metal complex catalyst of palladium having alkylphosphine as a ligand, (iii) a salt of the above metal complex catalyst. Further, in the present invention, the catalyst may be a solid-supported catalyst supported on a solid such as an activated carbon, polymer, inorganic solid (zeolite), or the like.

In the present invention, alkylphosphine is used as a catalyst compound in combination with the above-described palladium compound. Examples of specific compounds include exemplified compounds described below. Especially, t-Bu$^3$P is preferable in particular. In the present invention, the alkylphosphine may be suitable, so long as at least one organic group bonded to a phosphorus atom is an alkyl group. The remaining two groups may be a group other than the alkyl group. The alkylphosphine becomes a ligand for palladium. As mentioned above, a substance to which the alkylphosphine is previously coordinated may be used. Alternatively, both compounds may be added separately to a reaction system so that coordination is caused in the reaction system. In terms of handleability, it is preferable to use a salt that is formed by reacting these alkylphosphine and acid (although not limited in particular, for example, HBF$_4$, HBPh$_4$).

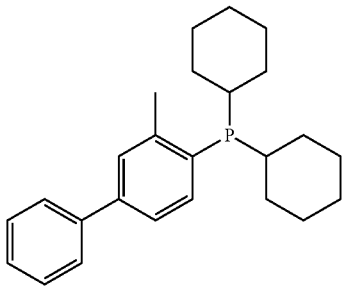

P-1

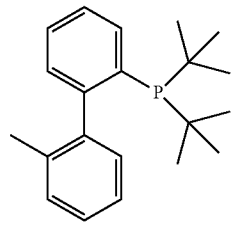

P-2

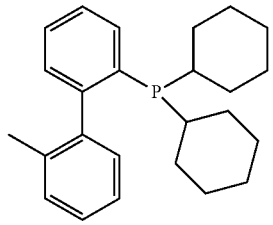

P-3

P-4

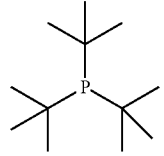

P-5

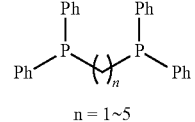

n = 1~5

P-6

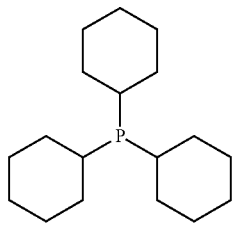

P-7

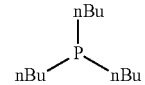

P-8

In the above formulae, Ph represents a phenyl group. nBu represents a n-butyl group.

Next, formula (1) is explained.

In the above-described formula, Ar$^1$, Ar$^2$ and Ar$^3$ each independently represent an aryl group or a heteroaryl group, each of which may be substituted. Examples of the substituent which may be substituted include the substituent group A described below. The number of carbon constituting $Ar^1$, $Ar^2$ or $Ar^3$ is preferably from 5 to 12. Among these, an aryl group is preferable. In this embodiment, the number of carbon constituting the aromatic ring is preferably from 6 to 12. A phenyl group is especially preferable. Further, $Ar^2$ and $Ar^3$ may be bonded to each other directly or through a linking group.

X represents a halogen atom substituted onto $Ar^1$, $Ar^2$, and/or $Ar^3$. However, if a plurality of X is present, the plurality of X may be the same or different halogen atom from each other. As the halogen atom, chlorine, bromine or iodine is preferable, bromine or iodine is more preferable, and bromine is most preferable, from the viewpoints of production cost and reaction properties to obtain an objective compound.

m represents a natural number, and preferably from 3 to 4.
<Substituent Group A>

Examples of the substituent group A include an alkyl group (preferably an alkyl group having 1 to 30 carbon atoms, more preferably 1 to 20 carbon atoms, and particularly preferably 1 to 10 carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having 2 to 30 carbon atoms, more preferably 2 to 20 carbon atoms, and particularly preferably 2 to 10 carbon atoms, e.g., vinyl, allyl, 2-butenyl, 3-pentenyl), an alkynyl group (preferably an alkynyl group having 2 to 30 carbon atoms, more preferably 2 to 20 carbon atoms, and particularly preferably 2 to 10 carbon atoms, e.g., propargyl, 3-pentynyl), an aryl group (preferably an aryl group having 6 to 30 carbon atoms, more preferably 6 to 20 carbon atoms, and particularly preferably 6 to 12 carbon atoms, e.g., phenyl, p-methylphenyl, naphthyl, anthranyl), an amino group (preferably an amino group having 0 to 30 carbon atoms, more preferably 0 to 20 carbon atoms, and particularly preferably 0 to 10 carbon atoms, e.g., amino, methylamino, dimethylamino, diethylamino, dibenzylamino, diphenylamino, ditolylamino), an alkoxy group (preferably an alkoxy group having 1 to 30 carbon atoms, more preferably 1 to 20 carbon atoms, and particularly preferably 1 to 10 carbon atoms, e.g., methoxy, ethoxy, butoxy, 2-ethylhexyloxy), an aryloxy group (preferably an aryloxy group having 6 to 30 carbon atoms, more preferably 6 to 20 carbon atoms, and particularly preferably 6 to 12 carbon atoms, e.g., phenyloxy, 1-naphthyloxy, 2-naphthyloxy), a heterocyclicoxy group (preferably a heterocyclicoxy group having 1 to 30 carbon atoms, more preferably 1 to 20 carbon atoms, and particularly preferably 1 to 12 carbon atoms, e.g., pyridyloxy, pyrazyloxy, pyrimidyloxy, quinolyloxy), an acyl group (preferably an acyl group having 1 to 30 carbon atoms, more preferably 1 to 20 carbon atoms, and particularly preferably 1 to 12 carbon atoms, e.g., acetyl, benzoyl, formyl, pivaloyl), an alkoxycarbonyl group (preferably an alkoxycarbonyl group having 2 to 30 carbon atoms, more preferably 2 to 20 carbon atoms, and particularly preferably 2 to 12 carbon atoms, e.g., methoxycarbonyl, ethoxycarbonyl), an aryloxycarbonyl group (preferably an aryloxycarbonyl group having 7 to 30 carbon atoms, more preferably 7 to 20 carbon atoms, and particularly preferably 7 to 12 carbon atoms, e.g., phenyloxycarbonyl), an acyloxy group (preferably an acyloxy group having 2 to 30 carbon atoms, more preferably 2 to 20 carbon atoms, and particularly preferably 2 to 10 carbon atoms, e.g., acetoxy, benzoyloxy), an acylamino group (preferably an acylamino group having 2 to 30 carbon atoms, more preferably 2 to 20 carbon atoms, and particularly preferably 2 to 10 carbon atoms, e.g., acetylamino, benzoylamino), an alkoxycarbonylamino group (preferably an alkoxycarbonylamino group having 2 to 30 carbon atoms, more preferably 2 to 20 carbon atoms, and particularly preferably 2 to 12 carbon atoms, e.g., methoxycarbonylamino), an aryloxycarbonylamino group (preferably an aryloxycarbonylamino group having 7 to 30 carbon atoms, more preferably 7 to 20 carbon atoms, and particularly preferably 7 to 12 carbon atoms, e.g., phenyloxycarbonylamino), a sulfonylamino group (preferably a sulfonylamino group having 1 to 30 carbon atoms, more preferably 1 to 20 carbon atoms, and particularly preferably 1 to 12 carbon atoms, e.g., methanesulfonylamino, benzenesulfonylamino), a sulfamoyl group (preferably a sulfamoyl group having 0 to 30 carbon atoms, more preferably 0 to 20 carbon atoms, and particularly preferably 0 to 12 carbon atoms, e.g., sulfamoyl, methylsulfamoyl, dimethylsulfamoyl, phenylsulfamoyl), a carbamoyl group (preferably a carbamoyl group having 1 to 30 carbon atoms, more preferably 1 to 20 carbon atoms, and particularly preferably 1 to 12 carbon atoms, e.g., carbamoyl, methylcarbamoyl, diethylcarbamoyl, phenylcarbamoyl), an alkylthio group (preferably an alkylthio group having 1 to 30 carbon atoms, more preferably 1 to 20 carbon atoms, and particularly preferably 1 to 12 carbon atoms, e.g., methylthio, ethylthio), an arylthio group (preferably an arylthio group having 6 to 30 carbon atoms, more preferably 6 to 20 carbon atoms, and particularly preferably 6 to 12 carbon atoms, e.g., phenylthio), a heterocyclicthio group (preferably a heterocyclicthio group having 1 to 30 carbon atoms, more preferably 1 to 20 carbon atoms, and particularly preferably 1 to 12 carbon atoms, e.g., pyridylthio, 2-benzimidazolylthio, 2-benzoxazolylthio, 2-benzothiazolylthio), a sulfonyl group (preferably a sulfonyl group having 1 to 30 carbon atoms, more preferably 1 to 20 carbon atoms, and particularly preferably 1 to 12 carbon atoms, e.g., mesyl, tosyl), a sulfinyl group (preferably a sulfinyl group having 1 to 30 carbon atoms, more preferably 1 to 20 carbon atoms, and particularly preferably 1 to 12 carbon atoms, e.g., methanesulfinyl, benzenesulfinyl), a ureido group (preferably a ureido group having 1 to 30 carbon atoms, more preferably 1 to 20 carbon atoms, and particularly preferably 1 to 12 carbon atoms, e.g., ureido, methylureido, phenylureido), a phosphoric acid amido group (preferably a phosphoric acid amido group having 1 to 30 carbon atoms, more preferably 1 to 20 carbon atoms, and particularly preferably 1 to 12 carbon atoms, e.g., diethylphosphoric acid amido, phenylphosphoric acid amido), a hydroxyl group, a mercapto group, a halogen atom (e.g., a fluorine atom, a chlorine atom, a bromine atom, an iodine atom; more preferably a fluorine atom), a cyano group, a sulfo group, a carboxyl group, a nitro group, a hydroxamic acid group, a sulfino group, a hydrazino group, an imino group, a heterocyclic group (preferably a heterocyclic group having 1 to 30 carbon atoms, and more preferably 1 to 12 carbon atoms; as hetero atoms, e.g., nitrogen, oxygen, sulfur; and specifically, e.g., imidazolyl, pyridyl, quinolyl, furyl, thienyl, piperidyl, morpholino, benzoxazolyl, benzimidazolyl, benzothiazolyl, carbazolyl, azepinyl), a silyl group (preferably a silyl group having 3 to 40 carbon atoms, more preferably 3 to 30 carbon atoms, and particularly preferably 3 to 24 carbon atoms, e.g., trimethylsilyl, triphenylsilyl), and a silyloxy group (preferably a silyloxy group having 3 to 40 carbon atoms, more preferably 3 to 30 carbon atoms, and particularly preferably 3 to 24 carbon atoms, e.g., trimethylsilyloxy, triphenylsilyloxy).

Specific examples of the compound represented by formula (1) are shown below. However, the present invention is not construed as being limited to these exemplified compounds.

1-1
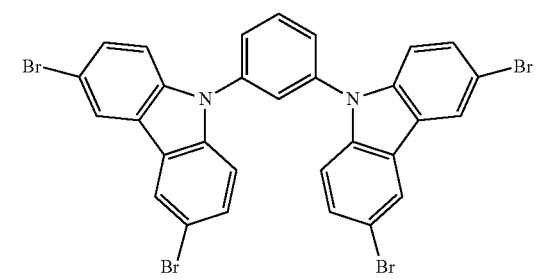
1-2
1-3
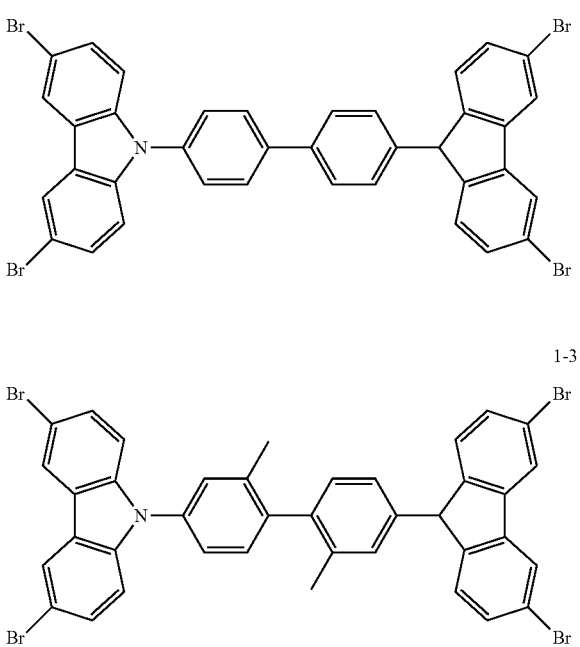
1-6
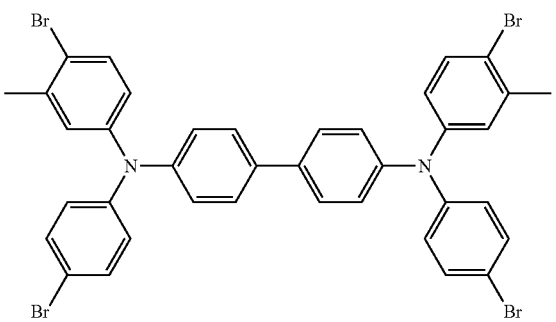
1-7
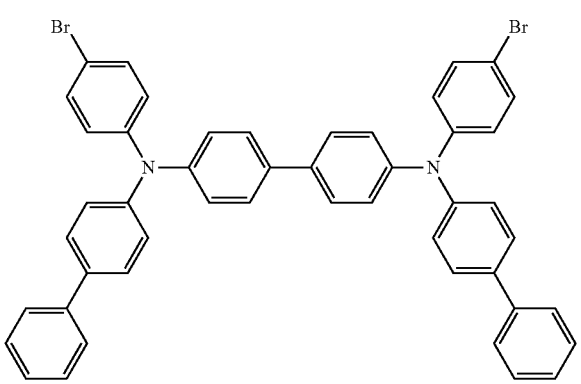
1-4
1-5
1-8
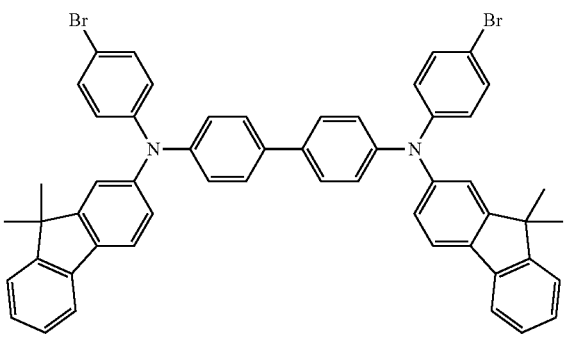
1-9
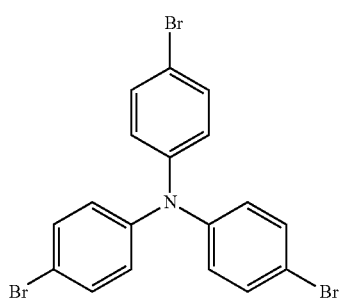

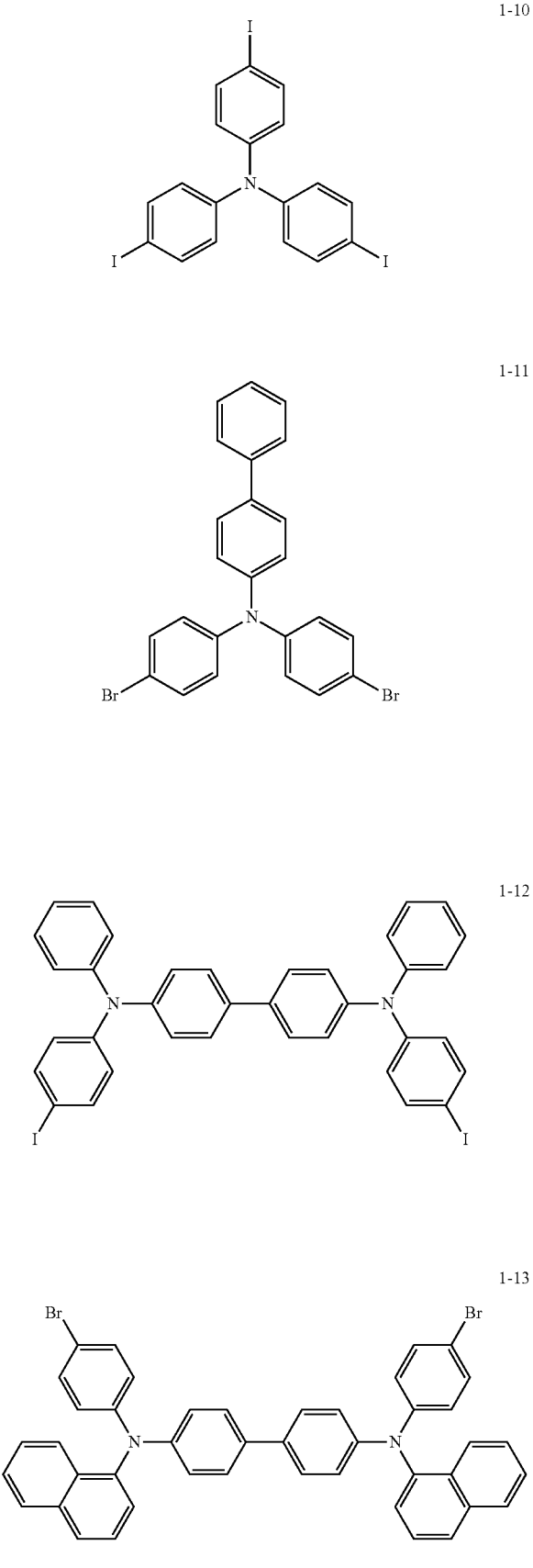

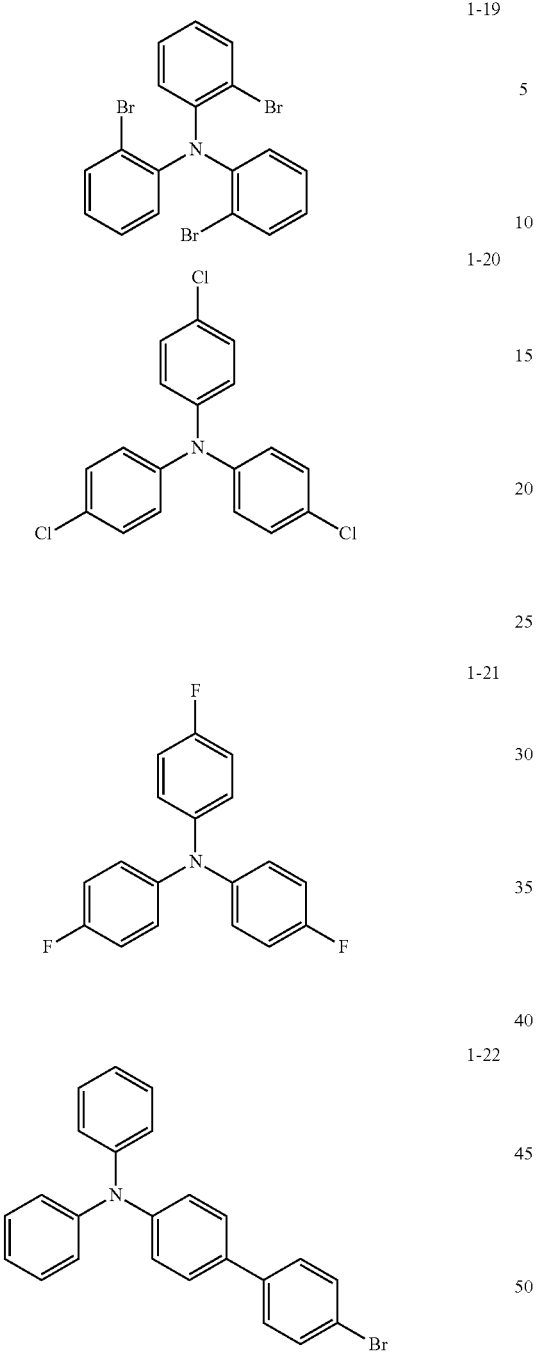

The above-described compound represented by formula (1) is preferably a compound represented by formula (5). In formula (5), Ar$^2$, Ar$^3$, Ar$^5$ and Ar$^6$ each independently represent an aryl group which may be substituted. A preferable range of the group is the same as those of Ar$^2$ and Ar$^3$ of formula (1). Further, Ar$^2$ and Ar$^3$, or Ar$^5$ and Ar$^6$ may be bonded to each other directly or through a linking group. Examples of the substituent which may be substituted include the above-described substituent group A: Ar$^4$ represents an arylene group which may be substituted. Examples of the substituent which may be substituted include the below-described substituent group A. Examples of the arylene group include groups described below. However, the arylene group is not limited thereto.

-continued 5-11

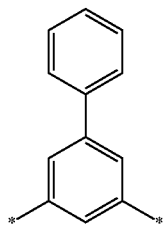

In these formulae, * indicates a bonding site.

Next, formula (2) is explained.

$R^1$, $R^2$ and $R^3$ each independently represent a hydrogen atom or a substituent. Examples of the substituent include the above-described substituent group A. $R^1$ and $R^2$ are preferably a hydrogen atom, an alkyl group, or an aryl group, more preferably a hydrogen atom, or an alkyl group, and most preferably a hydrogen atom. $R^3$ is preferably a substituent that is not a hydrogen atom, and preferably an alkoxy group (number of constitutional carbon is preferably 12 or less, more preferably 8 or less, and especially preferably 6 or less), an amino group (number of constitutional carbon is preferably 12 or less, more preferably 8 or less, and especially preferably 6 or less), an alkyl group (number of constitutional carbon is preferably 12 or less, more preferably 8 or less, and especially preferably 6 or less), an aryl group (number of constitutional carbon is preferably 12 or less, more preferably 8 or less, and especially preferably 6 or less), more preferably an alkoxy group or an amide, and especially preferably an alkoxy group. Specific compounds are shown below, but the present invention is not limited in the following exemplified compounds.

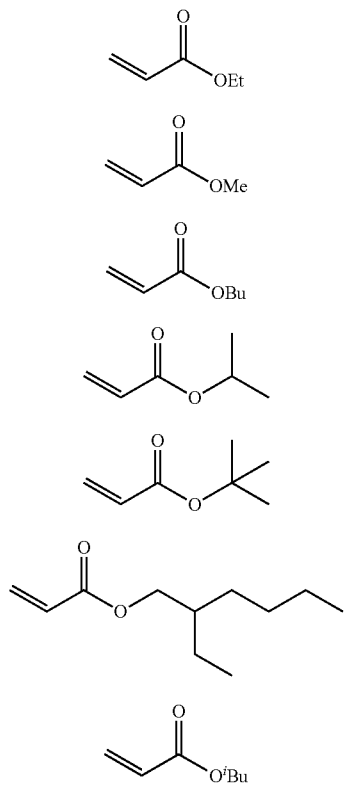

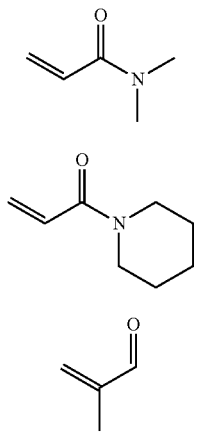

2-22

2-23

2-24

In the above-described formulae, Me represents a methyl group, Et represents a ethyl group, $^i$Bu represents an isobutyl group, n-Hexyl represents a n-hexyl group, n-Octyl represents a n-octyl group, and n-Decyl represents a n-decyl group.

In the above-described formula (3), $Ar^1$, $Ar^2$, $Ar^a$, X and m have the same meanings as those of formula (1), respectively. $R^{201}$, $R^{202}$ and $R^{203}$ have the same meanings as those of formula (2), respectively. n represents a natural number equal to or less than m, and n is preferably from 3 to 4.

Next, the conditions that exist when a compound represented by formula (1) is reacted with a compound represented by formula (2) are explained.

It is preferred that a base coexists in this reaction. As the base, it is possible to use inorganic bases (metal carbonate salts and metal alkoxides are exemplified. Though the metal is not particularly limited, potassium, sodium, cesium, rubidium and the like are preferable), or organic bases (examples include pyridine, diethylamine, triethylamine, diisopropylamine, diethylisopropylamine, dibutylamine, dicyclohexylamine, and DBU. Among these, diethylamine, triethylamine and diisopropylamine are preferable, and triethylamine is more preferable). Organic salts are preferable. As a use amount of the base, it is preferred to use the base of 1 or more equivalents relative to the equivalent of a side chain to be introduced. Further, when a base to be used is a liquid at a reaction temperature, the base may be used as a solvent.

In the present invention, a solvent is preferably used in the above-described reaction. Although the solvent is not particularly limited, examples of the solvent include aromatic solvents (toluene, xylene, chlorobenzene, orthodichlorobenzene, nitrobenzene, mesitylene, p-cymene, solvent naphtha, or the like are exemplified. Among these, toluene or xylene is preferable), aliphatic high boiling solvent (decane, or the like) and amide solvents (dimethyl formamide (DMF), dimethylacetamide (DMAc) and N-methylpyrrolidone (NMP) are exemplified. Among these, NMP is preferable). As a preferable solvent, aromatic solvents or amide solvents are preferable. Amide solvents are more preferable. Plural types of solvents may be used in combination thereof.

Although a reaction temperature is not particularly limited, the temperature is preferably from room temperature to 180° C., and more preferably from 70 to 160° C. The reaction temperature may be arbitrarily adjusted by checking a progress of the reaction with TLC (Thin Layer Chromatography) or HPLC (High-Performance Liquid Chromatography).

Although a reaction time is not particularly limited, the reaction is ordinarily carried out in a period of 5 minutes to 10 hours. The reaction time may be arbitrarily adjusted by checking a progress of the reaction with TLC or HPLC. As a post treatment, various types of refining operation may be carried out. It is possible to use properly extraction, column refinement, distillation, sublimation refinement, column chromatography, cleaning with a solvent, recrystallization, crystallization, or the like. The reaction may be carried out under atmosphere or inert atmosphere (nitrogen or a noble gas such as argon). The reaction is preferably carried out under inert atmosphere so that the catalyst is not inactivated.

A use amount of the above-described combination catalyst composed of palladium and alkylphosphine may be properly adjusted in accordance with an amount and kind of a reactive substrate. It is preferred to make the combination catalyst coexist within the reaction system in the range of 0.0001% by weight to 10% by weight with respect to the compound represented by formula (1).

It is preferred to obtain the above-described compound represented by formula (1) through halogenation of the above-described compound represented by formula (4). In formula (4), $Ar^1$, $Ar^2$ and $Ar^a$ have the same meanings as those of formula (1), respectively. Specific examples of the compound represented by formula (4) are shown below. However, the compound represented by formula (4) is not limited thereto.

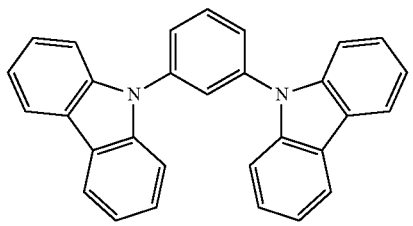

4-1

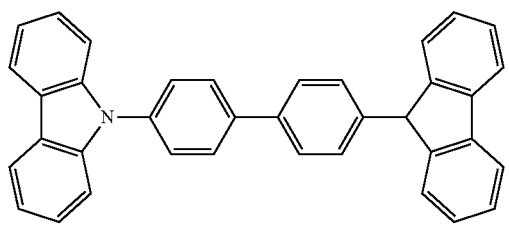

4-2

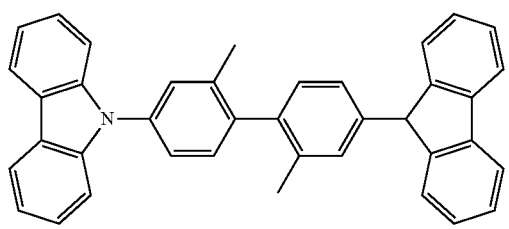

4-3

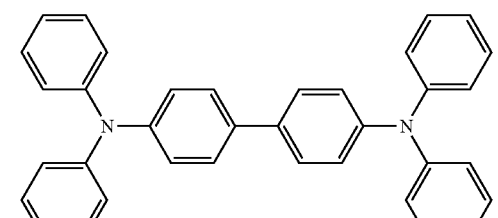

4-4

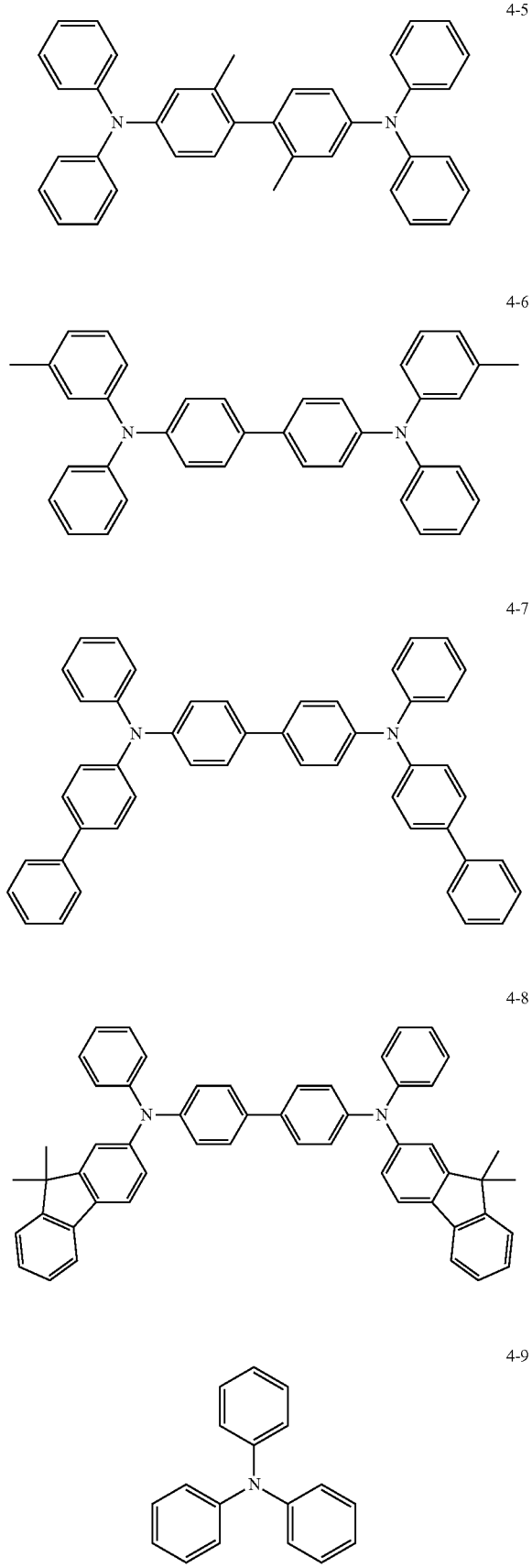

A method of producing the compound represented by formula (1) from the compound represented by formula (4) is explained.

As for the halogen atom that is used in halogenation, from the viewpoint of production cost and reactivity, as mentioned above, chlorination, bromination and iodination are preferable; bromination and iodination are more preferable; and bromination is especially preferable. Examples of the technique of conducting halogenation include a technique described in Jikken Kagaku Koza 5th Edition, Vol. 13, pages 341-474. Examples of the halogenating agent include halogen elemental substance (bromine, iodine, chlorine gas), a combination of metal halide (potassium halide, sodium halide, or the like) and an oxidant (peroxide salts such as sodium perchlorate, or the like), halogenated imides (For example, halogenated succinimide) and halogenated amides. It is also preferred to make peroxides coexist as an activating agent.

It is preferred that the above-described halogenation reaction is carried out using a solvent. Although the solvent is not particularly limited, examples of the solvent include aromatic solvents (chlorobenzene, orthodichlorobenzene, nitrobenzene, mesitylene, p-cymene, and solvent naphtha are exemplified. Among these, toluene or xylene is preferable); aliphatic high boiling solvent (decane, or the like); amide solvents (dimethyl formamide (DMF), dimethylacetamide (DMAc), N-methylpyrrolidone (NMP) are exemplified. Among these, NMP is preferable); halogen solvent (chloroform, dichloromethane, 1,2-dichloroethane 1,1,2-trichloroethane); and acetic acid. As a preferable solvent, amide solvents, halogen solvent or acetic acid are preferable. Amide solvents or acetic acid are more preferable. Plural types of solvents may be used in combination thereof.

Although a reaction temperature is not particularly limited, the temperature is preferably from −10° C. to 100° C., and more preferably from −5 to 80° C. The reaction temperature may be arbitrarily adjusted by checking a progress of the reaction with TLC or HPLC. Although a reaction time is not particularly limited, the reaction is ordinarily carried out in a period of 5 minutes to 10 hours. The reaction time may be arbitrarily adjusted by checking a progress of the reaction with TLC or HPLC. As a post treatment, various types of refining operation may be carried out. It is possible to use properly extraction, column refinement, distillation, sublimation refinement, column chromatography, cleaning with a solvent, recrystallization, crystallization, or the like. The reaction may be carried out under atmosphere or inert atmosphere (nitrogen or a noble gas such as argon).

The compound represented by formula (3) that is obtained by the production method of the present invention is useful for a raw compound (reaction intermediate) of an charge transportation material having a crosslinking group. That is, the triarylamine compound represented by formula (3) is produced, and then the substituent represented by —$C(R^1)$=$C(R^2)C$(=$O)R^3$ of the compound is modified to form a crosslinking group, whereby a compound that functions as an charge transportation material having a crosslinking group can be produced. Specifically, a residue of the compound represented by formula (2) ($\alpha,\beta$-unsaturated carbonyl substituent) introduced into the compound represented by formula (3) can be converted to a compound having an alcohol substituent (alcohol product), for example, by inducing the residue in the same manner as the conversion of from compound 203 to compound 205 shown in the above-described reaction scheme 1 and the below-described scheme 2. Using the alcohol product having a triarylamine skeleton, a compound having a predetermined crosslinking group is bonded to an alcohol substituent of the alcohol product whereby a triarylamine compound having a crosslinking group can be produced. The triarylamine compound having a crosslinking group is dissolved in a solvent to prepare a coating solution. The coating solution is coated to form a coating film. Thereafter, the crosslinking group is subjected to a crosslinking reaction to produce a crosslinked product of the triarylamine compound, whereby a thin film of tough electron transportation material can be obtained.

Examples of the crosslinking group include a functional group which progresses polymerization caused by a radical species, a cation species, an anion species, or like. Specific examples thereof include an acrylic group, a methacrylic group, an oxirane group, a vinyl group, and an oxethane group. The crosslinking group is preferably an acrylic group, a methacrylic group, and a vinyl group from the viewpoint of electric properties and mechanical strength after cross-linkage. As a method of introducing a substituent having such a crosslinking group, the following methods can be used. However, the present invention is not limited thereto.

<Method of Introducing of Acrylic Group, or Methacrylic Group>

These groups can be introduced by a technique such as (i) acid (paratoluene sulfonic acid or the like) catalytic dehydrocondensation between an alcohol part of the alcohol product of a compound having a triarylamine skeleton (for example, compound 205 in the scheme 2 described below) and acrylic (methacrylic) acid, (ii) condensation of an alcohol part of the alcohol product of a compound having a triarylamine skeleton (for example, compound 205 in the scheme 2 described below) and acrylic (methacrylic) acid chrolide, or (iii) ester exchange under the acid condition or basic condition between an alcohol part of the alcohol product of a compound having a triarylamine skeleton (for example, compound 205 in the scheme 2 described below) and acrylic (methacrylic) acid ester.

<Method of Introducing Oxirane Group>

The oxirane group can be introduced by performing a reaction between an alcohol part of the alcohol product of a compound having a triarylamine skeleton (for example, compound 205 in the scheme 2 described below) and (halogenomethyl)oxirane.

<Method of Introducing Vinyl Group>

The vinyl group can be introduced by performing a reaction between an alcohol part of the alcohol product of a compound having a triarylamine skeleton (for example, compound 205 in the scheme 2 described below) and styrene substituted with a halogenomethyl group on the benzene ring thereof in the presence of a base (potassium carbonate, or the like), thereby substituting the halogeno group.

<Method of Introducing Oxethane Group>

This group can be introduced by a technique such as (i) ester exchange reaction caused under the acidic or basic condition between an alcohol part of 3-ethyl-3-oxethane methanol and a —CO—$R^3$ part (for example, an ester part of compound 203 in the scheme 2 described below) of the compound represented by formula (3), (ii) dehydrocondensation of an alcohol part of 3-ethyl-3-oxethane methanol and a carboxylic acid to which a —CO—$R^3$ part (for example, an ester part of compound 203 in the scheme 2 described below) of the compound represented by formula (3) has been converted by hydrolysis under the acidic or basic condition, or (iii) condensation of an alcohol part of 3-ethyl-3-oxethane methanol and an acid chloride to which a —CO—$R^3$ part (for example, an ester part of compound 203 in the scheme 2 described below) of the compound represented by formula (3) has been converted.

The charge transporting material produced by using a triarylamine compound that is obtained according to the production method of the present invention may be applied to electronic devices or the like according to an ordinary method. Examples of the application include an embodiment in which the above-described crosslinking group-containing triarylamine compound is dissolved in a prescribed solvent to prepare a coating solution, and film production is performed using the coating solution so as to be a thin film according to a wet-type coating method that is ordinarily used for this type of materials. Thereafter, the above-described compound is subjected to crosslinking in the thin film whereby a high-intensity thin film having an charge transporting function can be obtained. For example, Japanese Patent Application Laid-open (JP-A) 2007-178813 or the like can be referred to for more information about such film production of the charge transporting material and application to devices in which the film is favorably used.

EXAMPLES

The present invention is further described in detail below with reference to Examples. However, the present invention is not construed as being limited thereto.

Example 1

Synthesis of Compound 202

97.7 g of compound 201 (the above-described Exemplified compound 4-4) (see reaction scheme 2 described below) and 1.5 L of NMP (N-methylpyrroridone) were added into a flask under the atmosphere, and heated at 80° C. 150 g of N-Bromosuccinimide was added to it frequently with a small amount. The reaction mixture was stirred at 80° C. for three hours. The reaction mixture was cooled to room temperature, and then 2.5 L of methanol was added. The precipitated powder was taken out by filtration. Thereby 133 g of compound 202 (the above-described Exemplified compound I-4) was obtained. The NMR spectrum of the obtained compound 202 is shown below.

$^1$H NMR: δ=6.95 (d, 8H), 7.12 (d, 4H), 7.37 (d, 8H), 7.44 (d, 4H) 300 MHz in CDCl$_3$

The same reaction as in the synthesis of compound 202 described above was conducted, except that toluene was used as the reaction solvent in place of NMP, and 1,3-dibrom-5,5-dimethylhydantoin was used as the brominating agent in place of N-bromosuccinimide. As a result, compound 202 was obtained equally.

(Synthesis of Compound 203)

30.0 g of compound 202 (compound represented by formula (1)), 24 mL of butyl acrylate (compound represented by formula (2)), 60 mL of triethylamine and 300 mL of NMP were added into a flask under nitrogen atmosphere, and heated at an outer temperature of 150° C. 0.32 g of t-Bu$_3$P.HBF$_4$ and 82 mg of palladium acetate were added to it and further stirred for two hours. The obtained reaction mixture was cooled to room temperature, and then 300 mL of aqueous hydrochloric acid was added to the reaction mixture. Then, extraction was conducted with ethyl acetate. The obtained organic layer was concentrated, and then a yellow powder was obtained by addition of hexane. The yellow powder was taken out by filtration thereby obtaining 31 g of compound 203 (compound represented by formula (3)). The NMR spectrum of the obtained compound 203 is shown below.

$^1$H NMR: δ=0.96 (t, 12H), 1.47 (tq, 8H), 1.68 (dt, 8H), 4.23 (t, 8H), 6.34 (d, 4H), 7.12 (d, 8H), 7.20 (d, 4H), 7.45 (d, 8H), 7.53 (d, 8H), 7.63 (d, 4H), 300 MHz in CDCl$_3$

The same reaction as in the synthesis of compound 203 described above was conducted, except that toluene was used as the reaction solvent in place of NMP. As a result, compound 203 was obtained equally.

(Synthesis of Compound 204) 31 g of compound 203, 1.7 g of palladium carbon, 32 g of ammonium formate, and 500 mL of isopropyl alcohol were added into a flask under the atmosphere, and stirred under the reflux condition for 1 hour. The obtained reaction mixture was subjected to sellite filtration, and then 500 mL of a salt solution was added to the filtrate. Then, extraction was conducted with ethyl acetate. The obtained organic layer was dried with sodium sulfate and concentrated, thereby obtaining 26.2 g of compound 204. The NMR spectrum of the obtained compound 204 is shown below.

$^1$H NMR: δ=0.94 (t, 12H), 1.38 (tq, 8H), 1.63 (dt, 8H), 2.63 (t, 8H), 2.92 (t, 8H), 4.10 (t, 8H), 7.00-7.15 (m, 20H), 7.42 (d, 4H) 300 MHz in CDCl$_3$ (Synthesis of Compound 205)

25.4 g of compound 204, 16.9 g of calcium chloride, and 200 mL of ethanol were added into a flask under the atmosphere, and then heated and stirred under the reflux condition. 11.5 g of sodium tetrahydroborate was added to it carefully and frequently with a small amount, and the mixture was stirred for 3 hours. The reaction mixture was cooled to room temperature, and then a concentrated hydrochloric acid was added to make the reaction mixture acidic. 500 mL of a salt solution and 300 mL of ethyl acetate were added to there to perform extraction. The collected organic layer was dried with sodium sulfate and concentrated. By refining using a silica gel column chromatography (toluene/ethanol=5/1), 13.3 g of compound 205 was obtained as a white solid. The NMR spectrum of the obtained compound 205 (alcohol product of triarylamine compound) is shown below.

$^1$H NMR: δ=1.72 (dd, 8H), 2.56 (t, 8H), 3.43 (dt, 8H), 4.47 (t, 4H), 6.90-7.00 (m, 12H), 7.14 (d, 8H), 7.49 (d, 4H) 300 MHz in DMSO-d6

(Synthesis of Compound 206)

8.75 g of compound 205, 8.6 mL of methacrylic acid, 1.9 g of paratoluene sulfonic acid monohydrate, and 100 mL of toluene were added to a flask under the atmosphere, and then heated and stirred at an external temperature of 160° C. for 1 hour, while removing water by Dean Stark apparatus. The reaction mixture was cooled to room temperature, and then the organic layer was washed twice with 100 mL of 5% sodium hydroxide aqueous solution, and once with 100 mL of a salt solution. The obtained organic layer was dried with sodium sulfate and concentrated. By refining using a silica gel column chromatography (hexane/ethyl acetate=5/1), 9.0 g of compound 206 (triarylamine compound having a crosslinking group) was obtained as a white solid. The NMR spectrum of the obtained compound 206 is shown below.

$^1$H NMR: δ=1.97 (s, 12H), 2.03 (tt, 8H), 2.69 (bs, 8H), 4.20 (t, 8H), 5.57 (s, 4H), 6.12 (s, 4H), 6.80-7.25 (bs, 20H), 7.33-7.53 (bs, 4H) 300 MHz in CDCl$_3$.

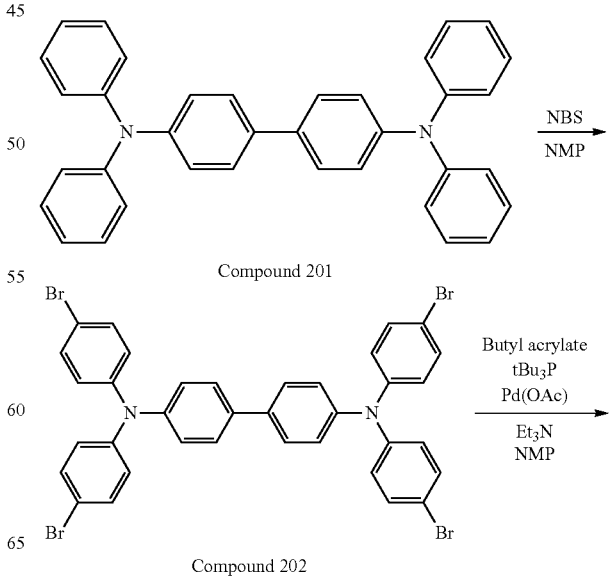

Scheme 2

Compound 201

NBS
NMP

Butyl acrylate
tBu$_3$P
Pd(OAc)
Et$_3$N
NMP

Compound 202

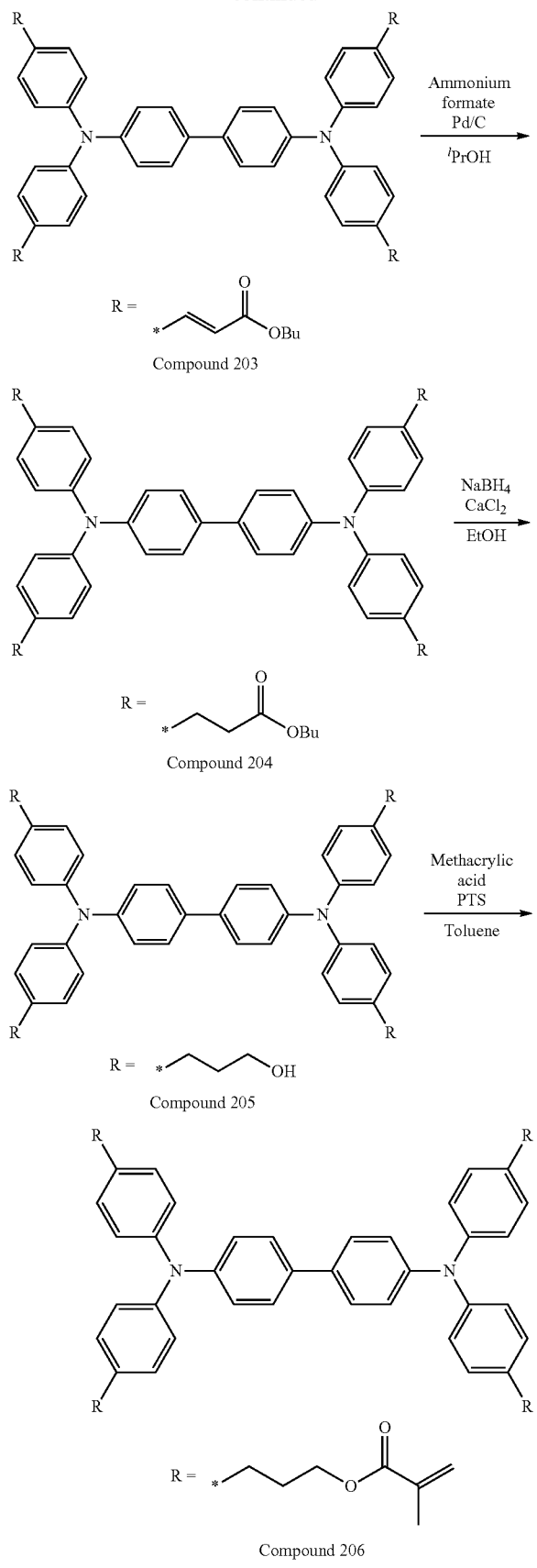

Examples 2 to 4, Comparative Examples 1, 2

Compound 203 was synthesized in the same manner as synthesis of compound 203 of the above-described Examples 1, except that the compound to be used in combination with palladium acetate was changed to t-Bu$_3$P·HBF$_4$ and substances shown in the following Table 1. As a result, in the synthesis using arylphosphine of Comparative Examples, production of compound 203 was not confirmed, whereas only in Examples 1 to 3, in which alkylphosphine was used, production of compound 203 was found.

TABLE 1

| Test No. | Ligand | Compound 203 | *Reaction time |
|---|---|---|---|
| Comparative Example 1 | PPh$_3$ | Not produced | C |
| Comparative Example 2 | Compound P-c1 described below | Not produced | C |
| Example 1 | t Bu$_3$P·HBF$_4$ | Produced | A |
| Example 2 | t Bu$_3$P | Produced | A |
| Example 3 | Exemplified compound P-1 described above | Produced | B |

*Reaction time
A represents less than 8 hours.
B represents from 8 hours to less than 50 hours.
C represents 50 hours or more.

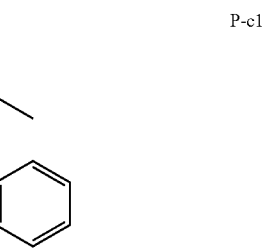

P-c1

The present invention has been explained together with its Examples. However, the present invention is not intended to be limited with respect to any details of the explanation, unless otherwise specified in particular. The present invention should be construed as broad as possible without going against the pit and marrow of the invention recited in claims attached herewith.

The invention claimed is:
1. A production method of a triarylamine compound, comprising the steps of:
providing a compound represented by following formula (5) and a compound represented by following formula (2); and
allowing the compound represented by formula (5) to react with the compound represented by formula (2) in the presence of palladium and alkylphosphine, to form a compound represented by following formula (6),

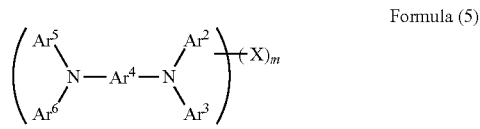

Formula (5)

Formula (2)

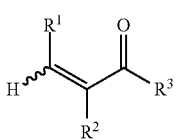

Formula (6)

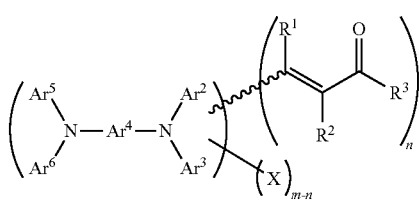

wherein, in formula (5), $Ar^2$, $Ar^3$, $Ar^5$, and $Ar^6$ each independently represent an aryl group which may have a methyl group, an ethyl group, a propyl group, and/or a butyl group; and $Ar^4$ represents an arylene group or a heteroarylene group, each of which may be substituted, selected from the group consisting of the following groups 5-1 to 5-11:

5-1

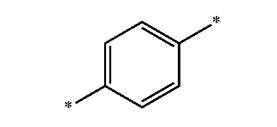

5-2

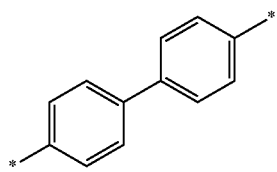

5-3

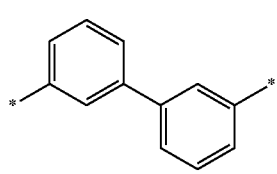

5-4

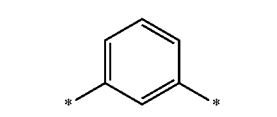

5-5

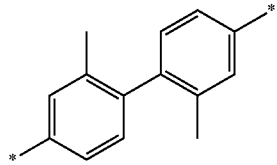

5-6

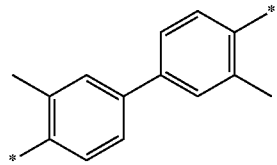

6-7

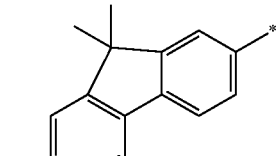

5-8

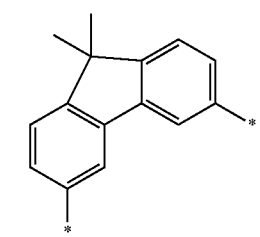

5-9

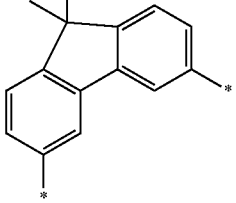

5-10

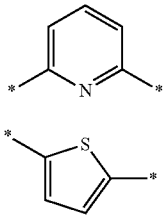

5-11

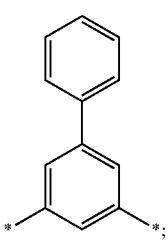

wherein, in the groups 5-1 to 5-11, * indicates a bonding site; X represents a halogen atom substituted onto $Ar^2$, $Ar^3$, $Ar^5$ and/or $Ar^6$; if a plurality of X is present, the plurality of X may be the same or different halogen atom from each other; and m is 3 to 4, wherein, in formula (2), $R^1$ represents a hydrogen atom or an alkyl group; $R^2$ represents a hydrogen atom or a methyl group; and $R^3$ represents a hydrogen atom, an alkoxy group, an aryl group, an amino group, or an alkyl group, and wherein, in formula (6), $Ar^2$, $Ar^3$, $Ar^5$, $Ar^6$, X and m have the same meanings as those of formula (5), respectively; $R^1$, $R^2$ and $R^3$ have the same meanings as those of formula (2), respectively; and n represents a natural number equal to or less than m.

2. A production method of a charge transporting material having a crosslinking group, comprising the steps of:
producing the compound represented by formula (6) through the method according to claim 1, and
modifying the substituent represented by —C($R^1$)=C($R^2$) C(=O)$R^3$ of the compound represented by formula (6) to form the crosslinking group.

3. The production method of a triarylamine compound according to claim 1 wherein, in formula (5), $Ar^2$, $Ar^3$, $Ar^5$ and $Ar^6$ each independently represent an aryl group having 6 to 12 carbon atoms and each may have a methyl group, an ethyl group, a propyl group, and/or a butyl group.

4. The production method of a triarylamine compound according to claim 3, wherein, in formulae (2) and (6), $R^1$ represents a hydrogen atom or an alkyl group; $R^2$ represents a hydrogen atom or a methyl group; and $R^3$ represents a hydrogen atom, an alkoxy group, an aryl group, an amino group, or an alkyl group.

5. The production method of a triarylamine compound according to claim 1 wherein, the compound represented by formula (2) is selected from the group consisting of formulae 2-1 to 2-24:

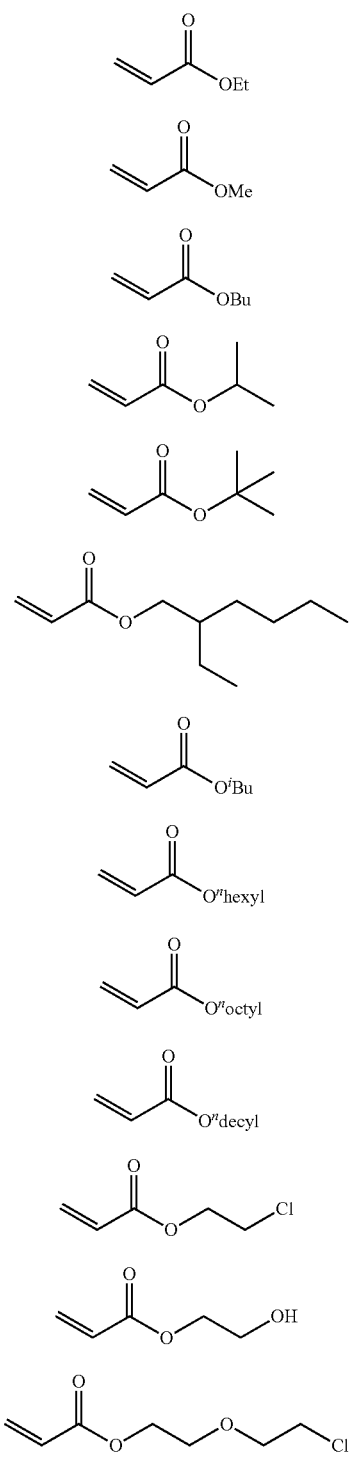

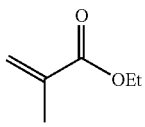
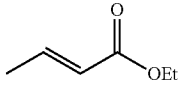
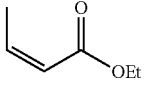
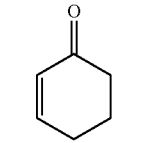
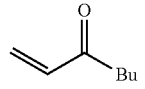
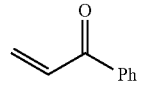
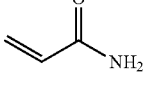
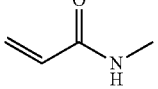
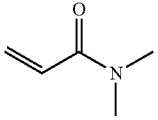
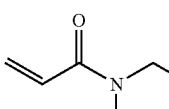
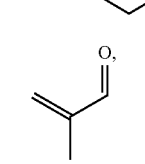

wherein Me represents a methyl group; Et represents an ethyl group; Bu represents an n-butyl group; $^i$Bu represents an isobutyl group; $^n$hexyl represents a n-hexyl group; $^n$octyl represents a n-octyl group; $^n$decyl represents a n-decyl group; and Ph represent a phenyl group.

6. The production method according to claim 1, wherein the compound represented by formula (5) is obtained by halogenation of a compound represented by following formula (7),

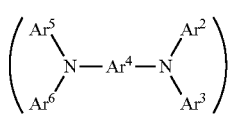

Formula (7)

wherein in formula (7), $Ar^2$, $Ar^3$, $Ar^4$, $Ar^5$, and $Ar^6$ have the same meanings as those of formula (5), respectively.

7. A production method of a triarylamine compound, comprising the steps of:
   providing the following compound 202 and butyl acrylate; and
   allowing compound 202 to react with butyl acrylate in the presence of palladium and alkylphosphine, to form the following compound 203, Compound 202

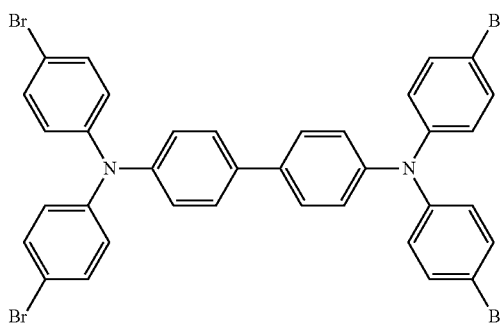

Compound 203

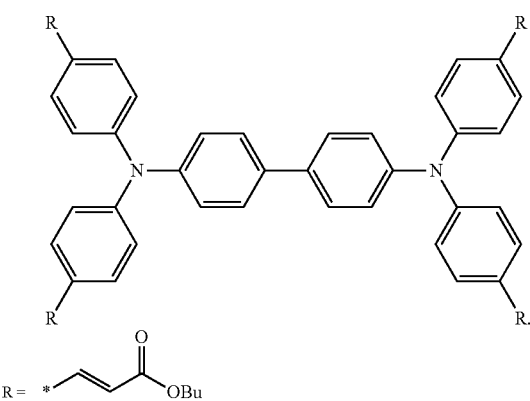

8. A production method of a triarylamine compound, comprising the steps of:
   providing a compound selected from the group consisting of formulae 1-1, 1-4 to 1-8, 1-12 to 1-14, 1-16 and 1-18 and a compound represented by formula (2); and
   allowing the compound selected from the group consisting of formulae 1-1, 1-4 to 1-8, 1-12 to 1-14, 1-16 and 1-18 to react with the compound represented by formula (2) in the presence of palladium and alkylphosphine,
   wherein, in formula (2), $R^1$ represents a hydrogen atom or an alkyl group; $R^2$ represents a hydrogen atom or a methyl group, and $R^3$ represents a hydrogen atom, an alkoxy group, an aryl group, an amino group, or an alkyl group, 1-1

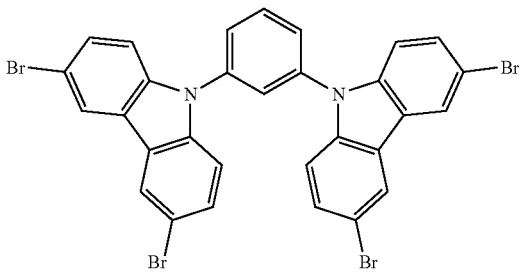

1-4

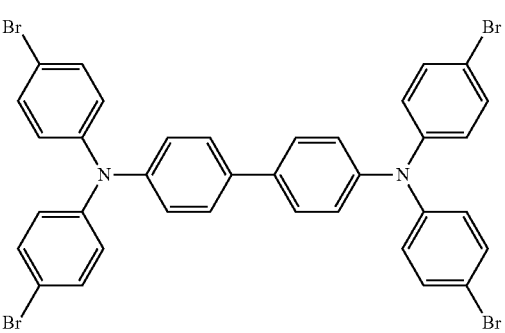

1-5

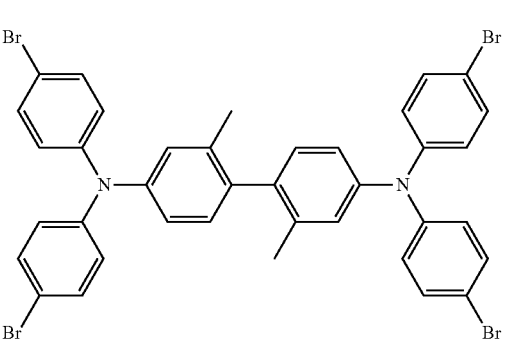

1-6

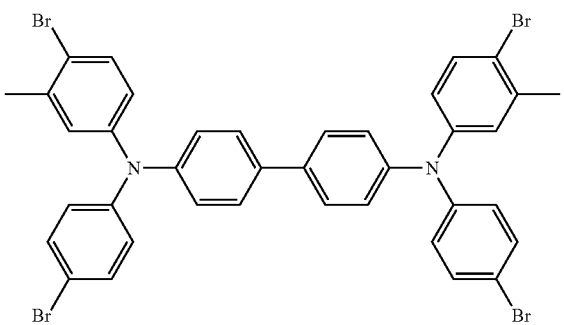

-continued
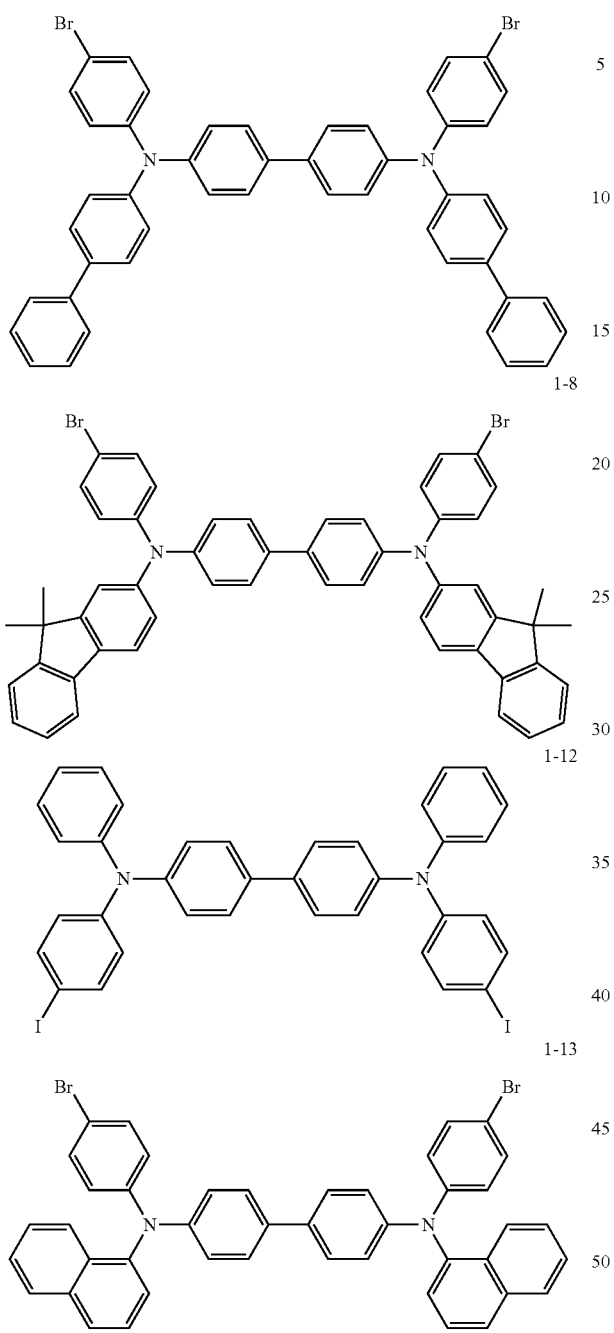
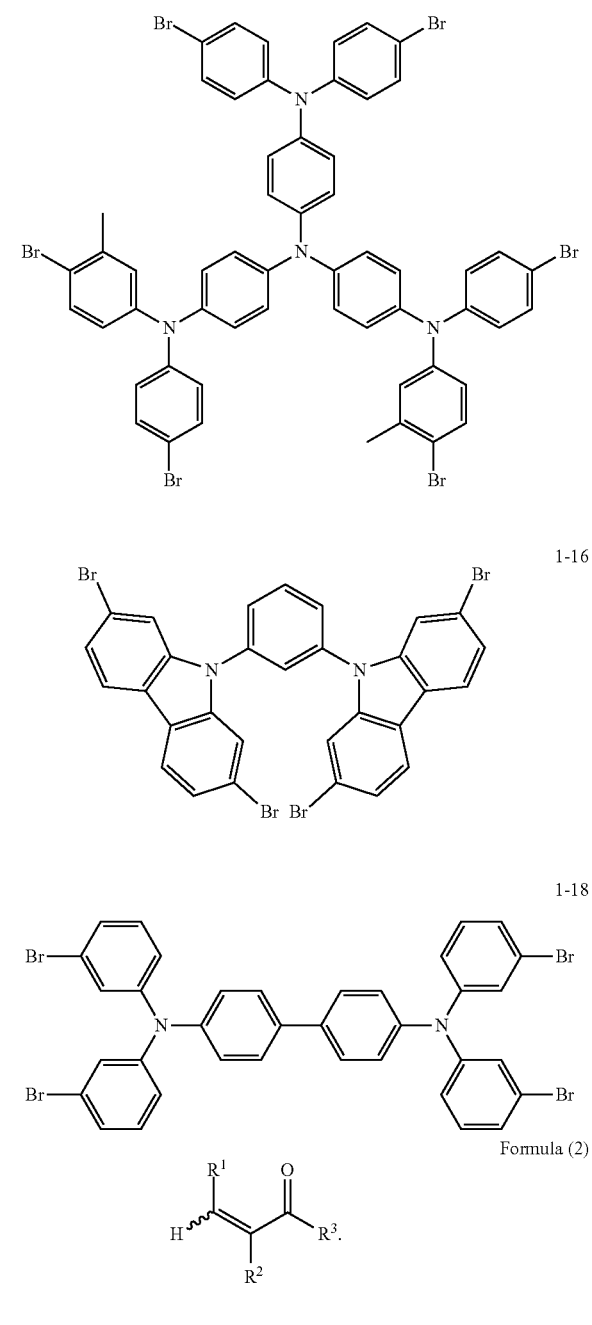
$$\underset{R^2}{\overset{R^1}{H}}\!\!\!=\!\!\!\underset{}{\overset{O}{\underset{}{\bigcup}}}\!\!R^3.$$
Formula (2)
* * * * *